(12) United States Patent
Pazenok et al.

(10) Patent No.: US 9,029,577 B2
(45) Date of Patent: May 12, 2015

(54) METHOD FOR PRODUCING METHYLENE-1,3-DIOXOLANES

(71) Applicant: Bayer Intellectual Property GmbH, Monheim (DE)

(72) Inventors: Sergii Pazenok, Solingen (DE); Albert Schnatterer, Leverkusen (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 14/375,816

(22) PCT Filed: Jan. 30, 2013

(86) PCT No.: PCT/EP2013/051756
§ 371 (c)(1),
(2) Date: Jul. 31, 2014

(87) PCT Pub. No.: WO2013/113738
PCT Pub. Date: Aug. 8, 2013

(65) Prior Publication Data
US 2014/0378690 A1   Dec. 25, 2014

(30) Foreign Application Priority Data

Feb. 1, 2012  (EP) .................................... 12153494

(51) Int. Cl.
*C07D 317/12*   (2006.01)
(52) U.S. Cl.
CPC ................................. *C07D 317/12* (2013.01)
(58) Field of Classification Search
CPC .................................................. C07D 317/12
USPC ........................................................ 549/430
See application file for complete search history.

(56) References Cited

U.S. PATENT DOCUMENTS 4,113,649 A   9/1978   Lehmkuhl et al.

FOREIGN PATENT DOCUMENTS

JP   2001302554 A   10/2001

OTHER PUBLICATIONS

International Search Report dated Jan. 30, 2013, issued in counterpart International Application No. PCT/EP2013/051756.
Mattay et al., Fragmentierung cyclischer Carboxonium-Ionen, IV Synthese von-Oxa-enonen, Journal of Organic Chemistry, XP055023167. pp. 1105-1117.
Ballou, Dihydroxyacetone Phosphate, Biochemical Preparations, University of California, 1960, pp. 45-50.
J. Org. Chem. 1987, 52, 2625-2627.
Goodman et al., Coupled, Vinyl and Acetal Ring-Opening Polymerization, Journal of Polymer Science: Part A, vol. 2, pp. 3471-3490 (1964).
Gevorkyan et al, Khimiya Geterocycl. Soed. N 1, 1991, pp. 33-36.
Gevorkyan et al , Khimiya Geterocycl. Soed. N 12, 1983, 1607-1613.

*Primary Examiner* — Taofiq A Solola
(74) *Attorney, Agent, or Firm* — Miles & Stockbridge PC

(57) ABSTRACT

The present invention relates to a novel method for preparing methylene-1,3-dioxolanes of the general formula (I)

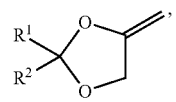

(I)

in which $R^1$ and $R^2$ have the meanings stated in the description. Methylene-1,3-dioxolanes are important intermediates for preparing pyrazoles and anthranilic acid amides, which may be used as insecticides.

6 Claims, No Drawings

METHOD FOR PRODUCING METHYLENE-1,3-DIOXOLANES

CROSS REFERENCE TO RELATED APPLICATIONS

This application is a §371 National Stage Application of PCT/EP2013/051756, filed Jan. 30, 2013, which claims priority to EP 12153494.5, filed Feb. 1, 2012.

BACKGROUND

1. Field of the Invention

The present invention relates to a novel method for preparing methylene-1,3-dioxolanes. Methylene-1,3-dioxolanes are important intermediates for preparing pyrazoles and anthranilic acid amides, which may be used as insecticides.

2. Description of Related Art

As previously described in the literature, 2-methylenedioxolanes may be prepared from 2-chloromethylenedioxolanes and KOH. It is reported in *Journal of Polymer Science* 1964, vol. 2 p.3471 and *Biochemical preparation,* 1960 v. 7, 45, that the reaction of 4-chloromethylene-1,3-dioxolanes with solid KOH affords only approx. 52% yield of the product (4-methylene-1,3-dioxolanes) and approx. 60% yield of 2,2-dimethyl-4-methylene-1,3-dioxolane. In contrast, Gevorkyan et al, *Khimiya Geterocycl. Soed.* N 1, 1991, pp. 33-36 report that KOH, when used as a solid or under phase transfer conditions, is not suitable for the dehydrochlorination of 2-chloromethyldioxolanes. For example, Gevorkyan et al. describe an isomerisation in which a shift in the double bond in the ring occurs. The elimination of HCl using anhydrous sodium diethylene glycolate (prepared from Na and diethylene glycol) was also proposed by Gevorkyan et al, *Khimiya Geterocycl. Soed.N* 12, 1983, 1607-1613, in which yields of approx. 70-80% can be achieved. The use of metallic sodium in an industurial setting is unfavourable for safety reasons. During the elimination of HCl some of the corresponding chloromethylenedioxolanes react with substitution of the chlorine atom by ethylene glycol anion, producing a high-boiling compound. It is reported in *J. Org. Chem,* 1987,52, 2625-27 that 2,2-dimethyl-4-methylene-1,3-dioxolane has only limited stability at −10° C. This indicates that the stability of the product is dependent on the production method.

In the methods described in the literature further disadvantages have been noted. The use of excess solid NaOH or KOH without solvent renders the reaction mixture impossible to stir, particularly towards the end of the reaction, after the product has been partly distilled off. It has additionally been observed that isomerisation occurs in the case of 2-methylene-4,4-dioxolane, particularly when the procedure is scaled up, where up to 5% of the corresponding isomer may form. Furthermore, the product partially decomposes under the reaction conditions with formation of acetone. This significantly influences the purity of the product, particularly on scale-up, which contains acetone residues. Up to 4% of acetone has been observed.

SUMMARY

The object of the present application is therefore to provide a novel method for preparing methylene-1,3-dioxolanes with high purity and yield, not having the disadvantages noted for the methods in the literature.

The object of the invention was solved by a method for preparing methylene-1,3-dioxolanes of the general formula (I),

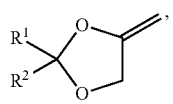

where
$R^1$ and $R^2$ independently of one another are hydrogen, alkyl, aryl or alkylaryl,
$R^1$ and $R^2$ may also form, together with the carbon atom to which they are linked, a 4- to 7-membered, saturated, optionally substituted ring,
by reacting compounds of formula (II),

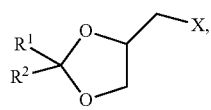

where
$R^1$, $R^2$ have the meanings stated above,
X is halogen,
with inorganic bases in the presence of polyethylene glycol dimethyl ethers or polyethylene glycol diethyl ethers.

DETAILED DESCRIPTION OF A PREFERRED EMBODIMENT

It may be considered surprising that the methylene-1,3-dioxolanes of formula (I) can be prepared selectively and in high yield by the method according to the invention without the troublesome side reactions such as ring-opening, isomerisation or substitution being observed.

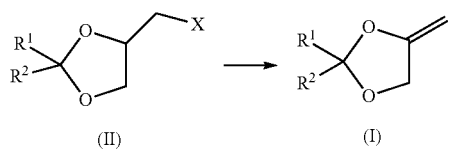

Examples of methylene-1,3-dioxolanes of formula (I) which can be prepared according to the inventive method are: 2,2-dimethyl-4-methylene-1,3-dioxolane, 4-methylene-1,3-dioxolane, 2,2-diethyl-4-methylene-1,3-dioxolane, 2,2-pentamethylene-4-methylene-1,3-dioxolane, 2,2-hexamethylene-4-methylene-1,3-dioxolane, 2-phenyl-4-methylene-1,3-dioxolane, 2-methyl-4-methylene-1,3-dioxolane.

GENERAL DEFINITIONS

In the context of the present invention, the term halogens (X) comprises, unless otherwise defined, those elements selected from the group consisting of fluorine, chlorine, bromine and iodine, with preference given to the use of fluorine, chlorine and bromine and particular preference to fluorine and chlorine. Substituted groups can be mono- or polysubstituted, where, in the case of polysubstitution, the substituents may be the same or different.

Alkyl groups substituted with one or more halogen atoms (—X) (=haloalkyl groups) are selected from, for example, trifluoromethyl ($CF_3$), difluoromethyl ($CHF_2$), $CCl_3$, $CFCl_2$, $CF_3CH_2$, $ClCH_2$, $CF_3CCl_2$.

In the context of the present invention, alkyl groups, unless otherwise otherwise defined, are linear or branched hydrocarbon groups.

The definition of alkyl and $C_1$-$C_{12}$-alkyl includes, for example, methyl, ethyl, n- and iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, alkylaryl groups (alkaryl groups), unless otherwise defined, are aryl groups substituted by alkyl groups, which can have a $C_{1-8}$ alkylene chain, while the aryl moiety may contain one or more heteroatoms, selected from O, N, P and S.

The compounds according to the invention can optionally be mixtures of various possible isomeric forms, particularly of stereoisomers such as E and Z isomers, threo and erythro isomers, as well as optical isomers, and also, if applicable, tautomers. Not only the E and Z isomers but also the threo and erythro isomers and the optical isomers and any mixtures of these isomers, as well as the possible tautomeric forms, are disclosed and claimed.

4-Halomethyl-1,3-dioxolane Derivates of Formula (II)

The 4-halomethyl-1,3-dioxolanes used as starting materials for carrying out the method according to the invention are generally defined by the formula (II)

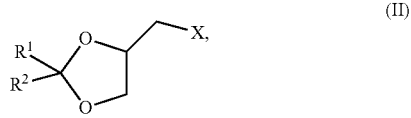

(II)

where $R^1$ and $R^2$ independently of one another are hydrogen, alkyl, aryl or alkylaryl, $R^1$ and $R^2$ may also form, together with the carbon atom to which they are linked, a 4- to 7-membered, saturated, optionally substituted ring, $R^1$ and $R^2$ independently of one another are preferably hydrogen, $(C_1$-$C_{12})$-alkyl, pentamethylene or hexamethylene, $R^1$ and $R^2$ particularly preferably are hydrogen, methyl, pentamethylene or hexamethylene, X is halogen, preferably chlorine or bromine, particularly preferably chlorine.

The compounds are known and may be prepared according to the methods as in *Journal of Polymer Science* 1964, vol. 2 p.3471; *Biochemical preparation*, 1960 v. 7, 45 and as described by Gevorkyan et al, *Khimiya Geterocycl. Soed. N* 1, 1991, pp. 37-39.

Examples of suitable starting materials according to the invention are 4-chloromethyl-2,2-dimethyl-1,3-dioxolane, 4-chloromethyl-1,3-dioxolane, 4-(chloromethyl)-2-methyl-1,3-dioxolane, 2-(chloromethyl)-1,4-dioxaspiro[4,4]nonane, 2-(chloromethyl)-1,4-dioxaspiro[4,5]decane, 4-(chloromethyl)-2-phenyl-1,3-dioxolane, 4-bromomethyl-2,2-dimethyl-1,3-dioxolane.

Reaction Procedure

The process step according to the invention is preferably carried out at a temperature ranging from 60° C. to 150° C., particularly preferably at temperatures of 80° C. to 140° C. The process step according to the invention is generally carried out at ambient pressure or under reduced pressure.

The reaction time is not critical and may be in a range from 1 hour to 2 or more hours, depending on the batch size and temperature.

In the process step according to the invention, 1 mole of the 4-halomethyl-1,3-dioxolane of formula (H) is reacted with 0.8 mole to 2.5 moles, preferably 1 mole to 2 moles, of an inorganic base. Suitable bases are NaOH, KOH, NaO$^t$Bu, KO$^t$Bu, NaOMe, KOMe. Particular preference is given to NaOH and KOH and very particular preference to NaOH.

The reaction is carried out in a solvent.

Suitable solvents are polyethylene glycol dimethyl ethers or polyethylene glycol diethyl ethers having a molar mass of 200 to 500. Particularly preferred are polyethylene glycol dimethyl ethers having a molar mass of 250.

Workup of the reaction mixture is carried out anhydrously by distillation of the product. The product is preferably distilled off directly from the reaction mixture. The distillation can also be carried out under reduced pressure in order to avoid additional thermal stress on the product. The residue (bottoms) may be further utilised after removal of salts, for example NaCl.

An aqueous workup is however also possible.

The purity of the compounds of formula (I) thus obtained is very high and is in the range of 97%-99%, and may be further utilised without a purification step. The reaction according to the invention is particularly notable due to the use of favourable raw materials, and also due to a simple, well controllable process also on an industrial scale.

The compounds of the general formula (I) are valuable intermediates in the synthesis of pyrazole acids, which in turn are important building blocks for the preparation of anthranilic acid amides having insecticidal activity (WO2007/112893, WO2007/144100). The compounds of formula (I) can be converted, for example, to pyrazole carboxylic acids according to scheme (1).

Scheme (I)

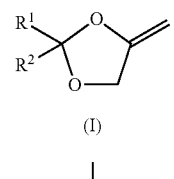

(I)

↓

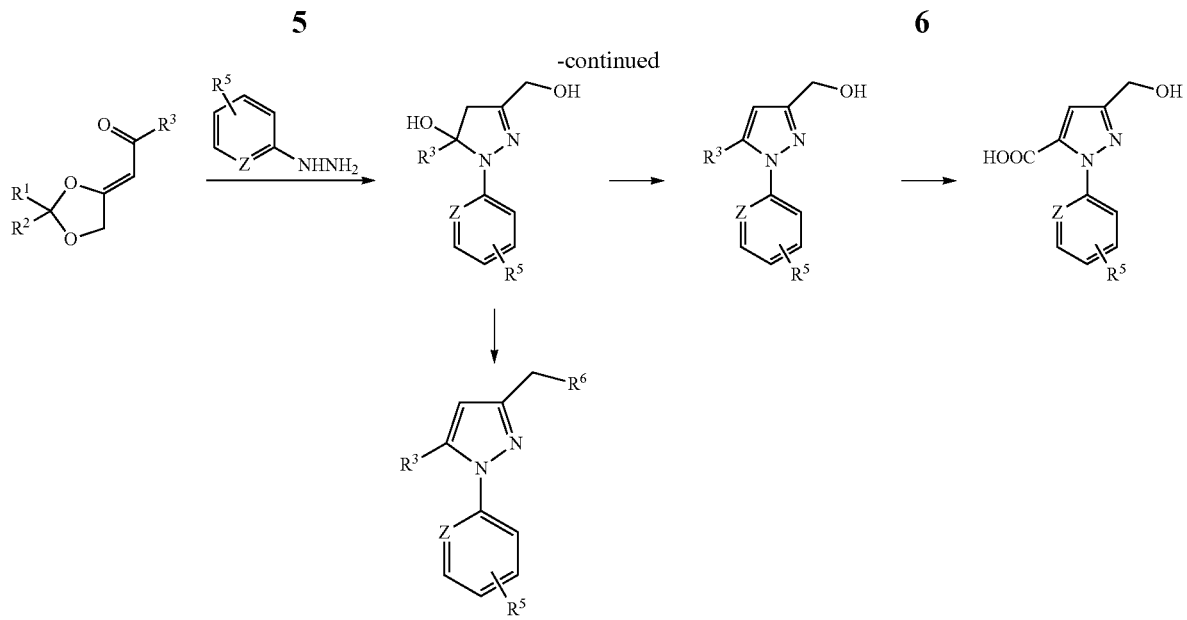

where
R¹, R² have the meanings stated above,
R³ is CX₃, (C=O)Oalkyl or (C=O)Oaryl,
X is halogen,
R⁵ is halogen, cyano, nitro, alkyl, cycloalkyl, haloalkyl, halocycloalkyl, alkoxy, haloalkoxy, alkylamino, dialkylamino, cycloalkylamino,
R⁶ is halogen, OSO₂Me, O(C=O)CH₃,
Z is CH, N.

WORKING EXAMPLES

The following working examples illustrate the invention without being limiting.

Example 1

2,2-Dimethyl-4-methylene-1,3-dioxolane

4-Chloromethyl-2,2-dimethyl-1,3-dioxolane (150 g, 1 mol) and 80 g of NaOH in 500 mL of polyethylene glycol dimethyl ether 250 were stirred for 2 hours at 120° C. After 2 hours, the GC sample showed complete conversion. A reduced pressure of 100 mbar was applied and the product was distilled off into a cooled receiver. 125 g (92%) of product was obtained with a purity of 99%.

B.p. 103-105° C.

Analytical characterisation:
$^1$H NMR (CDCl₃) δ:1.43 (s, 6H), 3.81 and 420 (dd, 2H), 4.7 (dd, 2H) ppm.

Example 2

4-Methylene-1,3-dioxolane

As described in example 1, though using 4-chloromethyl-1,3-dioxolane. The yield is 87%. B.p. 72-74° C. $n_d^{20}$1.4372 (see *Journal of Polymer Science* 1964, vol. 2 p.3487).

Example 3

2,2-Pentamethylene-4-methylene-1,3-dioxolane

As described in example 1, though using 4-chloromethyl-2,2-(pentamethylene)-1,3-dioxolane.

Yield 87%; B.p: 110-112° C. /50 mbar.

Analytical characterisation:
$^1$NMR (CDCl₃) δ:1.35-1.80 (m, 10H), 4.12 (br.s, 2H), 4.37-4.62 (m, 2H) ppm.

Example 4

2-Methyl-4-methylene-1,3-dioxolane

As described in example 1, though using 4-chloromethyl-2-methyl-1,3-dioxolane.

Yield 91%, B.p. 98-100° C.

Analytical characterisation:
$^1$H NMR: δ1.21 (d, 3H, Me), 3.75 (m, 1H, CH-Me), 4.1-4.5 (m, 2H, OCH₂), 4.80 (1H, CH=) 5.0 (1H, CH=) ppm.

The invention claimed is:
1. Method for preparing methylene-1,3-dioxolane of formula (I),

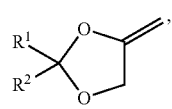
(I)

where
R¹ and R² independently of one another are hydrogen, alkyl, aryl or alkylaryl,
R¹ and R² may also form, together with the carbon atom to which they are linked, a 4- to 7-membered, saturated, optionally substituted ring,
comprising reacting a compound of formula (II),

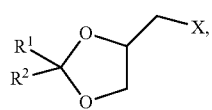
(II)

where $R^1$, $R^2$ have the meanings stated above,

X is halogen, with one or more inorganic bases in the presence of one or more polyethylene glycol dimethyl ethers or polyethylene glycol diethyl ethers.

2. Method for preparing a compound formula (I) according to claim 1, wherein $R^1$ and $R^2$ independently of one another are hydrogen, $(C_1-C_{12})$-alkyl, pentamethylene or hexamethylene, X is chlorine or bromine.

3. Method for preparing a compound formula (I) according to claim 1, wherein one or more of NaOH, KOH, NaO$^t$Bu, KO$^t$Bu, NaOMe or KOMe is used as inorganic base.

4. Method for preparing a compound of formula (I) according to claim 1, wherein one or more polyethylene glycol dimethyl ethers or polyethylene glycol diethyl ethers having a molar mass of 200 to 500 are used.

5. Method for preparing a compound formula (I) according to claim 1, wherein 1 mole of a compound of formula (II) is reacted with 0.8 mole to 2.5 moles of an inorganic base.

6. Method for preparing a compound of formula (I) according to claim 1, wherein the method is carried out in a temperature range from 60° C. to 150° C.

\* \* \* \* \*